(12) United States Patent
Temblay

(10) Patent No.: US 10,857,078 B2
(45) Date of Patent: Dec. 8, 2020

(54) POWDER ORAL HYGIENE COMPOSITIONS AND METHODS FOR THEIR MANUFACTURE

(71) Applicant: Swish IP Holdings Ltd., London (GB)

(72) Inventor: Anthony Cary Temblay, Vancouver (CA)

(73) Assignee: SWISH IP HOLDINGS LTD., London (GB)

( * ) Notice: Subject to any disclaimer, the term of this patent is extended or adjusted under 35 U.S.C. 154(b) by 0 days.

(21) Appl. No.: 16/483,232

(22) PCT Filed: Feb. 2, 2018

(86) PCT No.: PCT/GB2018/050301
§ 371 (c)(1),
(2) Date: Aug. 2, 2019

(87) PCT Pub. No.: WO2018/142146
PCT Pub. Date: Aug. 9, 2018

(65) Prior Publication Data
US 2020/0009025 A1 Jan. 9, 2020

(30) Foreign Application Priority Data

Feb. 4, 2017 (GB) .................................. 1701869.8

(51) Int. Cl.
| | |
|---|---|
| *A61K 8/04* | (2006.01) |
| *A61K 8/02* | (2006.01) |
| *A61K 8/25* | (2006.01) |
| *A61K 8/34* | (2006.01) |
| *A61K 8/36* | (2006.01) |
| *A61K 8/362* | (2006.01) |
| *A61Q 11/00* | (2006.01) |

(52) U.S. Cl.
CPC ............ *A61K 8/046* (2013.01); *A61K 8/0241* (2013.01); *A61K 8/25* (2013.01); *A61K 8/345* (2013.01); *A61K 8/36* (2013.01); *A61K 8/362* (2013.01); *A61Q 11/00* (2013.01); *A61K 2800/222* (2013.01)

(58) Field of Classification Search
CPC ................................ A61K 8/365; A61K 8/046
USPC ..................................................... 424/400, 52
See application file for complete search history.

(56) References Cited

U.S. PATENT DOCUMENTS

| | | | | |
|---|---|---|---|---|
| 4,374,824 | A | * | 2/1983 | Wahmi ..................... A61K 8/19 424/49 |
| 5,804,165 | A | | 9/1998 | Arnold |
| 5,817,294 | A | | 10/1998 | Arnold |
| 8,801,436 | B2 | | 8/2014 | Arnold |
| 2009/0253101 | A1 | | 10/2009 | Arnold |
| 2014/0227202 | A1 | * | 8/2014 | Pilgaonkar ........... A61K 8/0216 424/52 |
| 2015/0004560 | A1 | | 1/2015 | Arnold |

FOREIGN PATENT DOCUMENTS

| | | |
|---|---|---|
| WO | 00/33800 A | 6/2000 |
| WO | 00/33800 A1 | 6/2000 |
| WO | 2013/072932 A2 | 5/2013 |

OTHER PUBLICATIONS

International Search Report and Written Opinion issued by the European Patent Office dated Apr. 20, 2018 in International Application No. PCT/GB2018/050301 filed Feb. 2, 2018.

* cited by examiner

*Primary Examiner* — Walter E Webb
(74) *Attorney, Agent, or Firm* — Greenberg Traurig, LLP

(57) ABSTRACT

The invention provides a powder oral hygiene composition comprising xylitol, a source of carbon dioxide, an acid and an absorbent, wherein the composition has a water surface area greater than 160 $m^2/g$.

15 Claims, 4 Drawing Sheets

POWDER ORAL HYGIENE COMPOSITIONS AND METHODS FOR THEIR MANUFACTURE

PRIORITY INFORMATION

The present application is a 371 national phase application of International Application No. PCT/GB2018/050301 filed Feb. 2, 2018, which claims the benefit of Great Britain Provisional Application No. 1701869.8 filed 4 Feb. 2017, the entire contents and disclosures of which are hereby incorporated by reference.

FIELD OF THE INVENTION

This invention relates to powder oral hygiene compositions and methods for their manufacture. More particularly it relates to powder dentifrice compositions with specific water surface areas (WSAs) and to methods for their manufacture.

BACKGROUND OF THE INVENTION

The World Health Organization estimates that oral diseases are the fourth most expensive condition to treat—if a curative approach is taken, rather than a preventative approach. This is backed up by recent data from the Institute for Health Metrics and Evaluation's Global Burden of Disease Study (1990-2010) that identified untreated tooth decay as the most common condition amongst 291 diseases studied.

Oral health and general health are strongly linked. Dental disease contributes to, or exacerbates over twenty other significant systemic diseases. Research has associated dental disease with numerous conditions including diabetes, arthritis, cardio-vascular disease, cerebral-vascular disease, low-birth weight babies, premature births, premature aging and premature death.

Most preventable oral diseases start from a build up of bacterial induced bio-film, or plaque. Simply stated, controlling a patient's plaque enables the control and/or elimination of diseases of periodontal tissues (soft tissue) or of decay (hard tissue) and all the systemic diseases that follow. However, many countries do not have access to the most basic oral hygiene consumer products that prevent disease; even in developed countries, most individuals will be affected by oral diseases at some point in their lives. Oral diseases have a significant impact on the quality of life of individuals, their participation in society and economic productivity as well as on health systems, making oral diseases a significant public health concern.

The present invention may be used by patients and dental practitioners to improve a patient's oral hygiene and thereby reduce the impact of oral diseases on a patient's health.

Oral hygiene compositions, in the form of a powder containing an effervescent couple made up of a carbon dioxide source, such as sodium bicarbonate, and an acid, such as citric acid are known.

U.S. Pat. No. 5,817,294 discloses a dentifrice powder comprising an effervescent couple and a surfactant. After a small amount of the composition is placed in the mouth by the subject, the composition effervesces and is swished through the mouth for between 3 to 6 minutes, and then expelled or swallowed. Following the effervescent reaction, the surface of the mouth, tongue and teeth feels clean, substantially identical to the feeling experienced after brushing.

U.S. Pat. No. 5,804,165 describes several dentifrice tablets comprising an effervescent couple and the anti-caries agent, xylitol, as well as a single free flowing effervescent dentifrice powder composition. The tablet and powder composition also appear to have prevented the build up of plaque. According to the patent, the plaque removal and anti-plaque properties of the compositions are not fully understood. It is believed that when the composition is placed in the oral cavity, the saliva wets the composition, dissolving the bicarbonate, and the solubilized bicarbonate and acid in the resulting saliva mixture undergo a rapid acid-base reaction generating carbon dioxide gas in an effervescent reaction. The resulting salivary solution or paste is swept through the oral cavity, between the teeth, into crevices and cavities in between the teeth and into the junctions of the gums and the teeth. According to U.S. Pat. No. 5,804,165, it is believed that the bicarbonate, the acid, acid salt components and the acid-bicarbonate and carbonate salt components chemically loosen the plaque and organic and inorganic debris from the surface of the teeth and gums. After the effervescence has stopped, the resulting saliva mixture can be swished through the mouth to cleanse the surfaces of the teeth and gums (especially the surfaces between adjoining teeth) and to sweep out loose organic and inorganic debris. After expulsion or swallowing, it is believed that an appreciable amount of the solid bicarbonate-silica material adheres to the proteinaceous debris and mucosa which naturally resides on the surfaces of the teeth and gums. According to U.S. Pat. No. 5,804,165 plaque is adsorbed over time by the silica particles (adsorbents). No information is given about the rate at which the tablet or powder effervesces or how long it should be swished around the oral cavity before swallowing or expulsion.

U.S. Pat. No. 8,801,436, at example IX, describes a promising clinical study of pH changes after use of an effervescent dentifrice powder composition comprising an effervescent couple and xylitol. In this trial, each subject was placed the effervescent composition in the oral cavity and then expectorated after swishing the resulting salivary mixture for two minutes.

US 2015/0004560, which is a continuation in part of U.S. Pat. No. 8,801,436, describes a further effervescent 'powder oral rinse', Composition #2, comprising an effervescent couple and xylitol, as a component of tooth whitening kit.

We have found that the previously described oral hygiene powders comprising an effervescent couple and xylitol suffer from several disadvantages. The powders are slow to take up saliva in the mouth. In particular, they tend not to dissolve quickly in the mouth, but rather give a paste. This paste often has poor mouth feel; in particular, it can feel gritty, as though the powder contains sand.

We have now found a composition and methods for making such a composition which overcomes, or substantially mitigates these disadvantages.

SUMMARY OF THE INVENTION

Surprisingly, the inventors have found that the water surface area of such an effervescent composition has an effect on the dissolution of the formulation and its subsequent mouth feel. The inventors have also found that, surprisingly, this effect dose does not seem to be related to the particle size distribution of the powder components of the effervescent compositions. Such compositions can overcome the problems outlined above. Therefore, according to the invention, we provide a powder oral hygiene composition comprising xylitol, a source of carbon dioxide, an acid and an absorbent, wherein the composition has a water surface area greater than 160 m²/g.

We have found that such compositions are much more appealing to the general consumer. They have better, smoother and quicker dissolution which leads to easier acceptance to swallow the formulation, increasing efficacy. Eliminating the need to expel, allows consumers to use the formulation anywhere anytime socially or discreetly. This enhances the commercial viability and user adaptability of the composition greatly.

Without wishing to be bound by theory, it is thought that the extent of the water surface area of a particle shows a correlation to the surface hydrophilicity and consequently affects the dissolution behaviour of the particle. An increased surface hydrophilicity is thought to relate to an increased wettability characteristic, thus allowing for compositions according to the invention to show improved dissolution characteristics.

The water surface area of a sample may be determined from gravimetric vapour sorption (GVS) isotherms. A preferred model for the determining the water surface area is the Brunauer, Emmett and Teller (BET) model.

GVS is a method traditionally used to detect quantitative weight changes of samples as a function of the relative humidity (RH). Samples, which can comprise solid-state samples such as powders and tablets, but also liquids, are exposed to a defined humidity profile. The corresponding weight change is continuously recorded via an ultra-microbalance. Defined humidity levels are established by mixing defined ratios of a dry carrier gas, usually nitrogen, and a wet stream, typically a water vapour saturated carrier gas such as nitrogen. The RH level is then controlled by the ratio of the dry/wet stream. To maintain isothermal conditions, the GVS apparatus which comprises a microbalance and humidification unit is set up in an incubator system held at a defined temperature.

The primary information obtained by a typical commercial GVS system is the sorption isotherms. The equilibrium weight changes at each humidity are related to the dry mass of the sample (i.e. the equilibrium mass at 0% RH). The equilibrium weight changes as a function of the RH level are the corresponding sorption isotherms of the sample. Typical sorption isotherms comprise adsorption, i.e. increasing RH levels, and desorption, i.e. decreasing RH levels, cycles. Typically, RH ranges from 0-95% RH are covered.

Either the BET Model or the Excess Surface Work Model gas sorption models may be used to convert the GVS sorption data to actual water surface area data.

BET Model

The multilayer sorption model according to Brunauer, Emmet and Teller (Journal of the American Chemical Society, 60, pp. 309, (1938)) is described as follows:

$$\frac{n}{n_{mono}} = \frac{C \cdot \frac{p}{p_s}}{\left(1 - \frac{p}{p_s}\right) \cdot \left[1 + (C-1) \cdot \frac{p}{p_s}\right]} \Leftrightarrow \frac{\frac{p}{p_s}}{\left(1 - \frac{p}{p_s}\right) \cdot n} = \frac{1}{C \cdot n_{mono}} \cdot \left[1 + (C-1) \cdot \frac{p}{p_s}\right]$$

In which:
number of moles adsorbed at $p/p_s$ (=RH/100)
$n_{mono}$=apparent number of moles adsorbed in monolayer
$p/p_s$=gas partial pressure (=RH/100 in the GVS experiments)
C=BET constant (measure for the strength of the sorption interaction From the sorption kinetics, the equilibrium weight changes at the end of each RH stage are extracted to compile xy-data pairs (RH vs. adsorbed amount). This data corresponds to the following parameters in the BET equation (above):
$p/p_s$=water partial pressure, i.e. RH/100 in the GVS experiment
n=adsorbed amount, i.e. the detected weight change from the GVS experiment at each RH converted into the number of moles of water From this, a plot of $[p/p_s]/[n(1-p/p_s)]$ versus $p/p_s$ should give a linear correlation with intercept $b=1/[C(n_{mono})]$ and slope $m=b(C-1)$.

Evaluation is done by using 5-7 data points (RH vs. adsorbed amount) in the RH range 5-30% RH, which are then used for linear regression to obtain the intercept b and slope m (as explained above). The data is considered acceptable, if the correlation coefficient ($r^2$) of the linear regression is >0.95, although a correlation coefficient of ≥0.99 should be obtainable for most data sets. From slope and intercept, one can calculate the BET constant C and apparent monolayer amount $n_{mono}$.

Excess Surface Work Model

The xy-data pairs used for the sorption isotherms ($m_{RH}$, RH-levels) can also be used for a different approach to describe the sorption isotherm. Here, the change in chemical potential [Δμ] for the sorption process at each relative humidity (and at temperature T) is calculated:

$$\Delta\mu = RT \cdot \ln\left(\frac{p}{p_s}\right) = RT \cdot \ln\left(\frac{rh}{100}\right)$$

in which: R=Universal Gas Constant
T=Temperature
p=water partial pressure at humidity RH and temperature T
$p_s$=water vapour saturation pressure at temperature T
Δμ represents the change in chemical potential of the sorption process, since in equilibrium the chemical potential for the vapour phase equals the chemical potential of the adsorbed phase.

Based on the change in chemical potential Δμ, an energetic term Φ can be calculated for each relative humidity, termed excess surface work (ESW) according to J. Adolphs and MJ. Setzer, Journal of Colloid and Interface Science, 180, pp. 70-76, 1996:

$$\Phi = n_{ads} \cdot \Delta\mu$$

in which: Φ=excess surface work
Δμ=change in chemical potential
$n_{ads}$=number of moles of water adsorbed in equilibrium at humidity RH A plot of Φ/RT vs. $n_{ads}$ can then be generated, to allow the value of $n_{ads}$ at the minimum value of Φ/RT to be deduced. This value of $n_{ads}$ corresponds to $n_{mono}$.

Application of these gas sorption models for water vapour sorption data yielded the apparent monolayer coverage $n_{mono}$ for water vapour sorption processes, and further on, the water surface area parameter as used herein.

Water Surface Area

The calculated monolayer coverage $n_{mono}$ obtained from the application of the gas sorption models to GVS data can be re-calculated to water surface area $A_{water}$, taking into account the mean cross sectional area $a_{H20}$ occupied by one water molecule upon adsorption:

$$A_{water} = \frac{a_{H_2O} \cdot n_{mono} \cdot N_L}{m_{dry}(\text{sample})}$$

In which: $A_{water}$=water surface area [m²/g]
$A_{H20}$ mean cross sectional area of one water molecule adsorbed
=10⁻¹⁹ m²/molecule
$n_{mono}$=apparent amount adsorbed in the monolayer [mol]
$N_L$=Lochschmidt number=6×10²³ molecules/mol
$m_{dry}$ (sample)=dry mass of sample [g]

As an alternative, a non-gravimetric based sorption technique can be used to calculate the WSA. For example, a water partial pressure monitoring sorption system (such as that available from Quantachrome Instruments) may be used. In such a case the experiment is nearly the same, but as opposed to measuring the adsorbed amounts gravimetrically (via an ultra-microbalance), the adsorbed amounts are measured via water partial pressure measurements in defined cell volumes.

DETAILED DESCRIPTION OF THE INVENTION

The present invention may be used by patients and dental practitioners to improve a patient's oral hygiene and thereby reduce the impact of oral diseases on a patient's health.

The composition may comprise from about 30 wt % to about 95 wt % of xylitol, from about 3 wt % to about 60 wt % of a carbon dioxide source, from about 0.5 wt % to about 20 wt % of an adsorbent, and from about 0.5 wt % to about 15 wt % of an acid, wherein the components of the composition have a particle size of less than or equal to about 1410 microns. Optionally, the composition may comprise from about 40 wt % to about 95 wt % of xylitol, from about 50 wt % to about 95 wt % of xylitol, from about 60 wt % to about 95 wt %, from about 70 wt % to about 95 wt %, or from about 80 wt % to about 95 wt % xylitol. Optionally, the composition may comprise from about 3 wt % to about 50 wt %, from about 3 wt % to about 40 wt %, from about 3 wt % to about 30 wt %, from about 3 wt % to about 20 wt %, from about 3 wt % to 15 wt %, or from 3 wt % to about 9 wt % of a carbon dioxide source. Optionally, the composition may comprise from about 1 wt % to about 15 wt %, from about 1.5 wt % to about 12 wt %, from about 2 wt % to about 10 wt %, or from about 2.5 wt % to about 7 wt % of an adsorbent. Optionally, the composition may comprise from about 0.75 wt % to about 10 wt %, or from about 1 wt % to about 5 wt % of an acid. Optionally, the components of the composition have a particle size of less than or equal to about 950 microns, from 700 microns to about 900 microns, or about 850 microns. Optionally, the composition of the present invention comprises from about 80 wt % to about 95 wt % of xylitol, from about 3 wt % to about 9 wt % of a carbon dioxide source, from about 2.5 wt % to about 7 wt % of an adsorbent, and from about 1 wt % to about 5 wt % of an acid, wherein the components of the composition have a particle size of about 850 microns.

The composition of the present invention comprises natural ingredients and therefore it can be supplied as an over the counter (OTC) product.

Xylitol is commonly used as a sweetener. However, in certain concentrations, in combination with the carbon dioxide source, adsorbent, and acid, xylitol provides bactericidal activity against *Streptococcus mutans* (*S. mutans*), an anaerobic bacteria known to be involved in tooth decay in humans. *S. mutans* has also been implicated in serious systemic diseases. Thus, the composition of the present invention provides unexpectedly enhanced *S. mutans* reduction compared to what would be expected from xylitol alone. This is due to the synergistic effect of the xylitol, carbon dioxide source, adsorbent, and acid. This effect most likely occurs due to three properties conveyed to the xylitol by the combination of the carbon dioxide source, the adsorbent, and the acid. These include: (1) increased surfactant activity; (2) pH buffered in the mildly basic region; and (3) substansivity of xylitol.

The carbon dioxide source may be non-aqueous, water soluble and pharmaceutically acceptable, for example, a carbonate (and salts thereof), a bicarbonate (and salts thereof), and mixtures thereof. More specifically, the carbon dioxide source may be selected from lithium carbonate, lithium bicarbonate, sodium carbonate, sodium bicarbonate, potassium carbonate, potassium bicarbonate, calcium carbonate, magnesium carbonate, ammonium carbonate and ammonium bicarbonate, and combinations thereof. Optionally, the carbon dioxide source is sodium bicarbonate.

The adsorbent may act as a plaque adsorbent. The adsorbent may be a metal oxide or salts thereof. The metal oxide may be selected from silica, alumina, aluminosilicate and zircon, and salts and combinations thereof. Optionally, the adsorbent is silica.

The acid may be non-aqueous, water soluble and pharmaceutically acceptable, for example, an organic acid, in particular, the fruit acids. The acid may be selected from citric acid, tartaric acid, fumaric acid and malic acid, and combinations thereof. Optionally, the acid is citric acid.

The composition may comprise the following combinations of components: xylitol, lithium carbonate, silica and citric acid; xylitol, lithium bicarbonate, silica and citric acid; xylitol, sodium carbonate, silica and citric acid; xylitol, sodium bicarbonate, silica and citric acid; xylitol, potassium carbonate, silica and citric acid; xylitol, potassium bicarbonate, silica and citric acid; xylitol, calcium carbonate, silica and citric acid; xylitol, magnesium carbonate, silica and citric acid; xylitol, ammonium carbonate, silica and citric acid; xylitol, ammonium bicarbonate, silica and citric acid; xylitol, lithium carbonate, alumina and citric acid; xylitol, lithium bicarbonate, alumina and citric acid; xylitol, sodium carbonate, alumina and citric acid; xylitol, sodium bicarbonate, alumina and citric acid; xylitol, potassium carbonate, alumina and citric acid; xylitol, potassium bicarbonate, alumina and citric acid; xylitol, calcium carbonate, alumina and citric acid; xylitol, magnesium carbonate, alumina and citric acid; xylitol, ammonium carbonate, alumina and citric acid; xylitol, ammonium bicarbonate, alumina and citric acid; xylitol, lithium carbonate, aluminosilicate and citric acid; xylitol, lithium bicarbonate, aluminosilicate and citric acid; xylitol, sodium carbonate, aluminosilicate and citric acid; xylitol, sodium bicarbonate, aluminosilicate and citric acid; xylitol, potassium carbonate, aluminosilicate and citric acid; xylitol, potassium bicarbonate, aluminosilicate and citric acid; xylitol, calcium carbonate, aluminosilicate and citric acid; xylitol, magnesium carbonate, aluminosilicate and citric acid; xylitol, ammonium carbonate, aluminosilicate and citric acid; xylitol, ammonium bicarbonate, aluminosilicate and citric acid; xylitol, lithium carbonate, zircon and citric acid; xylitol, lithium bicarbonate, zircon and citric acid; xylitol, sodium carbonate, zircon and citric acid; xylitol, sodium bicarbonate, zircon and citric acid;

xylitol, potassium carbonate, zircon and citric acid; xylitol, potassium bicarbonate, zircon and citric acid; xylitol, calcium carbonate, zircon and citric acid; xylitol, magnesium carbonate, zircon and citric acid; xylitol, ammonium carbonate, zircon and citric acid; xylitol, ammonium bicarbonate, zircon and citric acid; xylitol, lithium carbonate, silica and tartaric acid; xylitol, lithium bicarbonate, silica and tartaric acid; xylitol, sodium carbonate, silica and tartaric acid; xylitol, sodium bicarbonate, silica and tartaric acid; xylitol, potassium carbonate, silica and tartaric acid; xylitol, potassium bicarbonate, silica and tartaric acid; xylitol, calcium carbonate, silica and tartaric acid; xylitol, magnesium carbonate, silica and tartaric acid; xylitol, ammonium carbonate, silica and tartaric acid; xylitol, ammonium bicarbonate, silica and tartaric acid; xylitol, lithium carbonate, alumina and tartaric acid; xylitol, lithium bicarbonate, alumina and tartaric acid; xylitol, sodium carbonate, alumina and tartaric acid; xylitol, sodium bicarbonate, alumina and tartaric acid; xylitol, potassium carbonate, alumina and tartaric acid; xylitol, potassium bicarbonate, alumina and tartaric acid; xylitol, calcium carbonate, alumina and tartaric acid; xylitol, magnesium carbonate, alumina and tartaric acid; xylitol, ammonium carbonate, alumina and tartaric acid; xylitol, ammonium bicarbonate, alumina and tartaric acid; xylitol, lithium carbonate, aluminosilicate and tartaric acid; xylitol, lithium bicarbonate, aluminosilicate and tartaric acid; xylitol, sodium carbonate, aluminosilicate and tartaric acid; xylitol, sodium bicarbonate, aluminosilicate and tartaric acid; xylitol, potassium carbonate, aluminosilicate and tartaric acid; xylitol, potassium bicarbonate, aluminosilicate and tartaric acid; xylitol, calcium carbonate, aluminosilicate and tartaric acid; xylitol, magnesium carbonate, aluminosilicate and tartaric acid; xylitol, ammonium carbonate, aluminosilicate and tartaric acid; xylitol, ammonium bicarbonate, aluminosilicate and tartaric acid; xylitol, lithium carbonate, zircon and tartaric acid; xylitol, lithium bicarbonate, zircon and tartaric acid; xylitol, sodium carbonate, zircon and tartaric acid; xylitol, sodium bicarbonate, zircon and tartaric acid; xylitol, potassium carbonate, zircon and tartaric acid; xylitol, potassium bicarbonate, zircon and tartaric acid; xylitol, calcium carbonate, zircon and tartaric acid; xylitol, magnesium carbonate, zircon and tartaric acid; xylitol, ammonium carbonate, zircon and tartaric acid; xylitol, ammonium bicarbonate, zircon and tartaric acid; xylitol, lithium carbonate, silica and fumaric acid; xylitol, lithium bicarbonate, silica and fumaric acid; xylitol, sodium carbonate, silica and fumaric acid; xylitol, sodium bicarbonate, silica and fumaric acid; xylitol, potassium carbonate, silica and fumaric acid; xylitol, potassium bicarbonate, silica and fumaric acid; xylitol, calcium carbonate, silica and fumaric acid; xylitol, magnesium carbonate, silica and fumaric acid; xylitol, ammonium carbonate, silica and fumaric acid; xylitol, ammonium bicarbonate, silica and fumaric acid; xylitol, lithium carbonate, alumina and fumaric acid; xylitol, lithium bicarbonate, alumina and fumaric acid; xylitol, sodium carbonate, alumina and fumaric acid; xylitol, sodium bicarbonate, alumina and fumaric acid; xylitol, potassium carbonate, alumina and fumaric acid; xylitol, potassium bicarbonate, alumina and fumaric acid; xylitol, calcium carbonate, alumina and fumaric acid; xylitol, magnesium carbonate, alumina and fumaric acid; xylitol, ammonium carbonate, alumina and fumaric acid; xylitol, ammonium bicarbonate, alumina and fumaric acid; xylitol, lithium carbonate, aluminosilicate and fumaric acid; xylitol, lithium bicarbonate, aluminosilicate and fumaric acid; xylitol, sodium carbonate, aluminosilicate and fumaric acid; xylitol, sodium bicarbonate, aluminosilicate and fumaric acid; xylitol, potassium carbonate, aluminosilicate and fumaric acid; xylitol, potassium bicarbonate, aluminosilicate and fumaric acid; xylitol, calcium carbonate, aluminosilicate and fumaric acid; xylitol, magnesium carbonate, aluminosilicate and fumaric acid; xylitol, ammonium carbonate, aluminosilicate and fumaric acid; xylitol, ammonium bicarbonate, aluminosilicate and fumaric acid; xylitol, lithium carbonate, zircon and malic acid; xylitol, lithium bicarbonate, zircon and malic acid; xylitol, sodium carbonate, zircon and malic acid; xylitol, sodium bicarbonate, zircon and malic acid; xylitol, potassium carbonate, zircon and malic acid; xylitol, potassium bicarbonate, zircon and malic acid; xylitol, calcium carbonate, zircon and malic acid; xylitol, magnesium carbonate, zircon and malic acid; xylitol, ammonium carbonate, zircon and malic acid; xylitol, ammonium bicarbonate, zircon and malic acid; xylitol, lithium carbonate, silica and malic acid; xylitol, lithium bicarbonate, silica and malic acid; xylitol, sodium carbonate, silica and malic acid; xylitol, sodium bicarbonate, silica and malic acid; xylitol, potassium carbonate, silica and malic acid; xylitol, potassium bicarbonate, silica and malic acid; xylitol, calcium carbonate, silica and malic acid; xylitol, magnesium carbonate, silica and malic acid; xylitol, ammonium carbonate, silica and malic acid; xylitol, ammonium bicarbonate, silica and malic acid; xylitol, lithium carbonate, alumina and malic acid; xylitol, lithium bicarbonate, alumina and malic acid; xylitol, sodium carbonate, alumina and malic acid; xylitol, sodium bicarbonate, alumina and malic acid; xylitol, potassium carbonate, alumina and malic acid; xylitol, potassium bicarbonate, alumina and malic acid; xylitol, calcium carbonate, alumina and malic acid; xylitol, magnesium carbonate, alumina and malic acid; xylitol, ammonium carbonate, alumina and malic acid; xylitol, ammonium bicarbonate, alumina and malic acid; xylitol, lithium carbonate, aluminosilicate and malic acid; xylitol, lithium bicarbonate, aluminosilicate and malic acid; xylitol, sodium carbonate, aluminosilicate and malic acid; xylitol, sodium bicarbonate, aluminosilicate and malic acid; xylitol, potassium carbonate, aluminosilicate and malic acid; xylitol, potassium bicarbonate, aluminosilicate and malic acid; xylitol, calcium carbonate, aluminosilicate and malic acid; xylitol, magnesium carbonate, aluminosilicate and malic acid; xylitol, ammonium carbonate, aluminosilicate and malic acid; xylitol, ammonium bicarbonate, aluminosilicate and malic acid; xylitol, lithium carbonate, zircon and malic acid; xylitol, lithium bicarbonate, zircon and malic acid; xylitol, sodium carbonate, zircon and malic acid; xylitol, sodium bicarbonate, zircon and malic acid; xylitol, potassium carbonate, zircon and malic acid; xylitol, potassium bicarbonate, zircon and malic acid; xylitol, calcium carbonate, zircon and malic acid; xylitol, magnesium carbonate, zircon and malic acid; xylitol, ammonium carbonate, zircon and malic acid; and xylitol, ammonium bicarbonate, zircon and malic acid.

The combination of the carbon dioxide source, the adsorbent, and the acid act together with xylitol to reduce surface tension. This surface tension reduction may be due to: (a) the adsorbent affecting the hydrogen bonding and hydrophobic effects exerted on the surface of the salivary matrix formed when the composition is placed in a subject's mouth, thus causing for a weaker overall hydrogen bonding; (b) the slightly basic pH due to the carbon dioxide source as well as an overall reduction in the intermolecular water hydrogen bonding potential of the salivary matrix. The surface active effects of the combination of the carbon dioxide source, the adsorbent, and the acid appear to complement and enhance any surface active effects of xylitol, and since the intercellular attachment of bacteria to each other as well as the surfaces of the soft and hard tissues as well as the dental plaque surfaces are important for the vitality of the *S. mutans*, reducing the amount and strength of the many types of chemical bonding attachment enhances the anti-caries activity.

A number of reports have been published that describe the bacteriostatic activity of xylitol on *S. mutans* (the strain of bacteria that have been shown to be the main cause of dental caries) and its relationship to the observed effects. In the present invention, synergy between the xylitol and the combination of the carbon dioxide source, the adsorbent, and the acid may provide for an unobvious enhancement of the bacteriostatic effects observed. This may be due to the extracellular pH as well as the above-described enhanced surface activity. The combination of the carbon dioxide source, the adsorbent, and the acid may act as a pH-buffer. The consequence of the pH buffering as well as the enhanced reduction of extracellular and cellular surface tension may allow for a higher intracellular concentration of xylitol, and thus a more pronounced anti-caries effect due to increased kinetics of the specific enzymatic mechanism comprising the bacteriostatic biochemistry of xylitol.

The composition is prepared such that upon usage, it causes the salivary pH to remain in the basic range, and that the pH is sustained in the basic range at least 10 minutes after usage. More particularly, it has been observed that pH increases to above pH 8 within 1 minute after the composition has been placed in a subject's mouth. The pH remains above pH 7.4 for at least about 10 minutes, and then gradually declines to a normal neutral pH of about 7 within 60 minutes.

Substantivity of the xylitol also results from the synergy of xylitol and the combination of the carbon dioxide source, the adsorbent, and the acid. This may be due to the binding of the xylitol to the adsorbent particles present. As explained above, the pH of the saliva remains in the mildly basic region for up to an hour after using the composition of the present invention.

This suggests that the xylitol is also sustained in the mouth after the composition has been placed in a subject's mouth. The activity of xylitol is directly related to the amount of xylitol present in the mouth, which may reflect the amount of xylitol inside bacterial cells. Therefore, having an appreciable amount of xylitol remaining in the mouth provides for increased activity. In addition, the subject is provided with an enhanced cosmetic effect, since a sweet and soothing mouth feel and aftertaste lasts for many minutes.

The composition may be in the form of an effervescent powder. Effervescence occurs due to carbon dioxide being released when the carbon dioxide source dissolves in the water present in saliva and reacts with the acid. For example, in compositions comprising sodium bicarbonate and citric acid, the sodium bicarbonate dissolves in the water present in saliva then reacts with the citric acid to release carbon dioxide.

The composition may be used to introduce additional beneficial substances to the oral cavity. These additional beneficial substances may provide oral health or other health benefits. These additional beneficial substances may pass through the oral mucosa or via the stomach into the bloodstream and hence to the entire body. Therefore, the composition may further comprise additional components. Optionally the additional components comprise flavouring agents.

The composition of the present invention is easy to use. According to another aspect of the present invention there is provided the use of the composition of the present invention, wherein said use comprises:
(i) placing the composition in a subject's mouth;
(ii) sealing the subject's lips;
(iii) allowing the composition to form a salivary mixture with the subject's saliva;
(iv) moving the salivary mixture around the subject's mouth; and
(v) optionally, swallowing the salivary mixture.

In embodiments in which the composition of the present invention is provided in stick packs, placing the composition in a subject's mouth may comprise pouring the composition out of an open stick pack onto the subject's tongue.

Moving the salivary mixture around the subject's mouth may comprise swirling the salivary mixture around the subject's mouth using the tongue and cheek muscles to manipulate the salivary mixture.

Use of the composition of the present invention aids in the control of oral pH, controls the levels of plaque and food debris present in the subject's mouth, and aids in the control and reduction of growth of harmful bacteria that is implicated in oral diseases and halitosis, as well as systemic diseases related to the presence of the bacteria. It has also been found that use of the composition of the present invention aids in the removal of bio-film (comprising organic and inorganic materials that accumulate in the form of dental plaque) from the enamel and gingiva. Further, as mentioned above, the composition of the present invention aids in remineralisation of the teeth (with or without remineralisation agent).

Optionally, the composition of the present invention may be used at least once a day, and may be used after eating.

According to other aspects of the present invention there is provided the composition of the present invention for use in preventing tooth decay, removing plaque, treating gingivitis and/or treating halitosis. The composition may be used to prevent tooth decay, remove plaque, treat gingivitis and/or treat halitosis in a mammal, such as a dog or a human.

According to other aspects of the present invention there is provided a method of preventing tooth decay, removing plaque, treating gingivitis and/or treating halitosis, wherein the method of treatment comprises placing the composition of the present invention in a subject's mouth. The composition may be used in a method of preventing tooth decay, removing plaque, treating gingivitis and/or treating halitosis in a mammal, such as a dog or a human.

According to another aspect of the present invention there is provided a method of manufacturing the composition of the present invention, wherein the method comprises:
(i) combining the desired wt % of the xylitol, the carbon dioxide source and the acid to form a first mixture;
(ii) grinding the first mixture to so that the components of the first mixture have a desired particle size; and
(iii) adding the desired wt % of the adsorbent with a desired particle size.

Preferably the composition is ground so that it is able to pass through a 250 micron sieve, such as US #60 mesh size.

EXAMPLES

Figure 1:
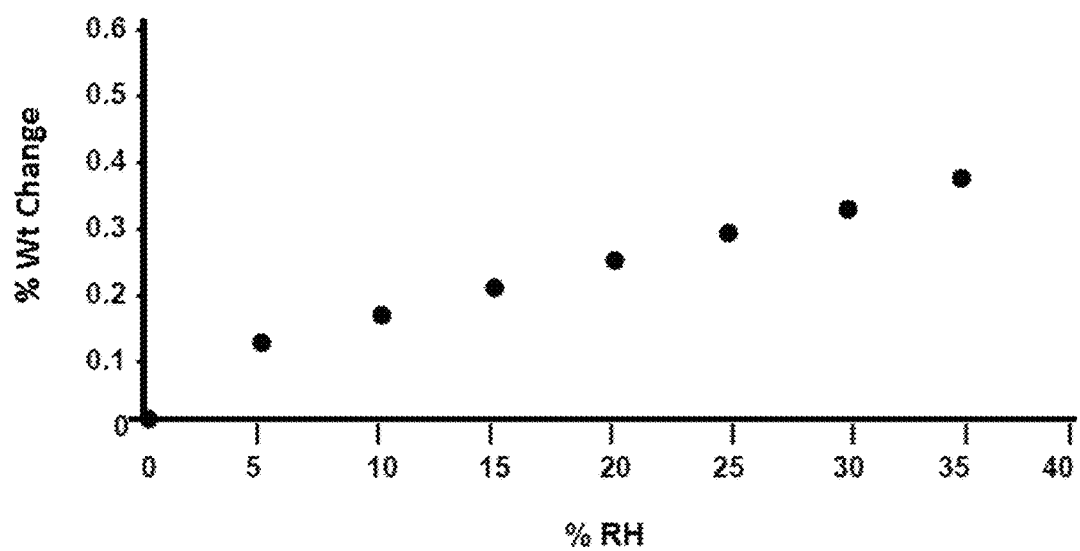
FIG. 1 is a GVS isotherm of a prior art composition similar to that described in US 2015/0004560, for convenience referred to as WOW Pink
Figure 2:
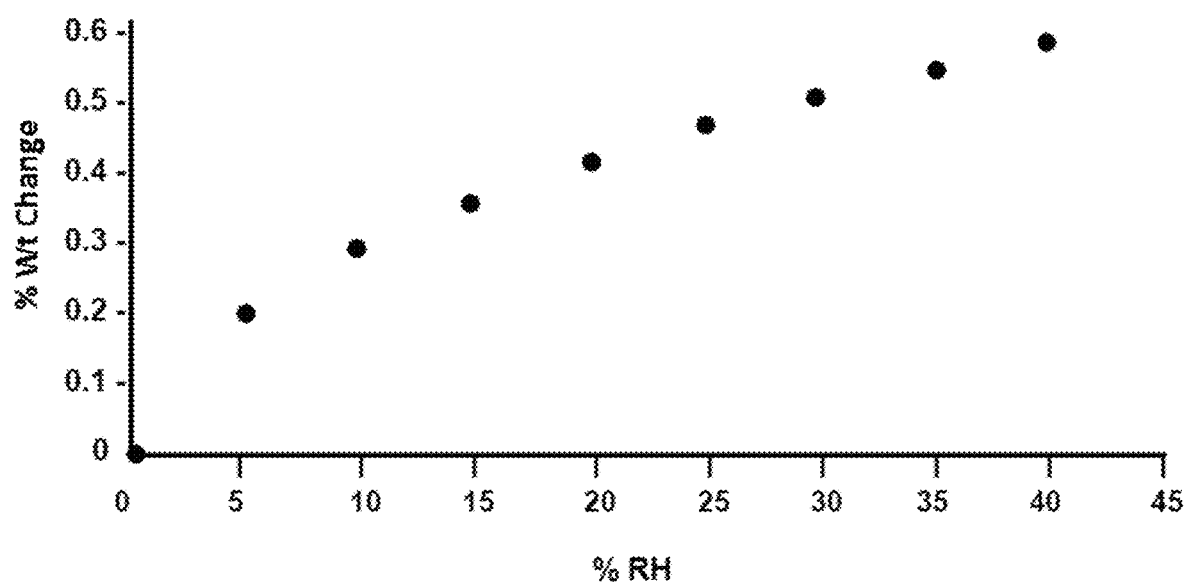
FIG. 2 is a GVS isotherm of a composition according to the invention, as described in the Example, for convenience referred to as SWISH
Figure 3:
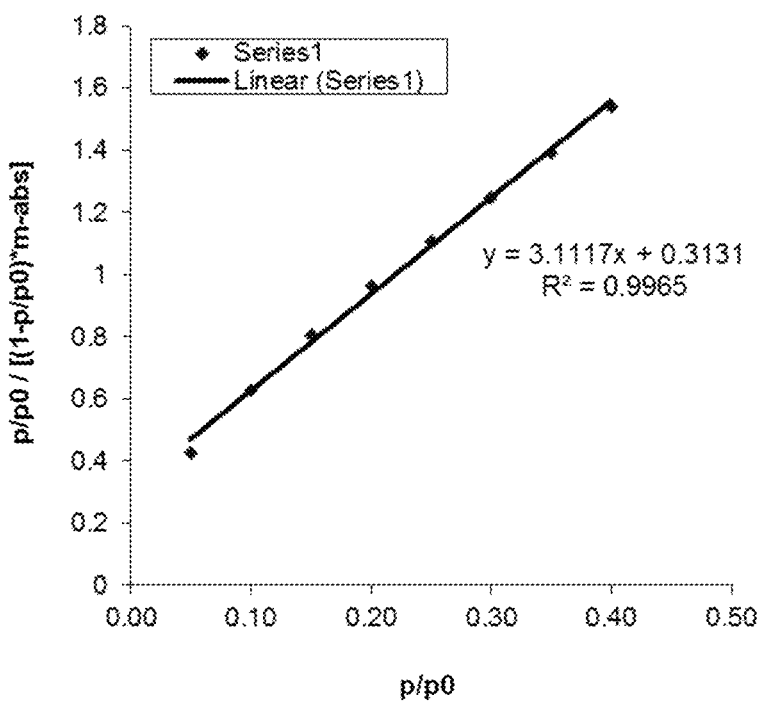
FIG. 3 is a BET plot for WOW Pink based on the GVS data in FIG. 1
Figure 4:
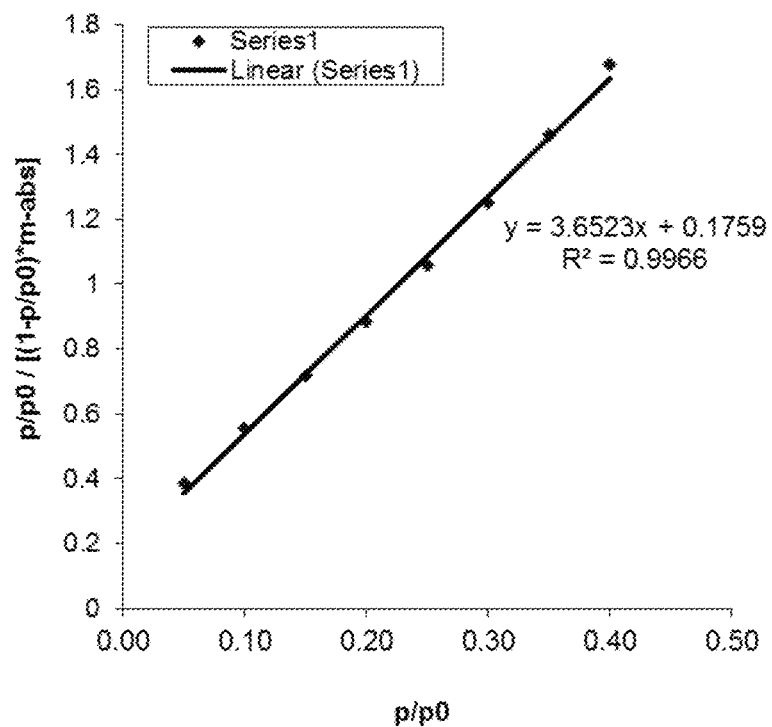
FIG. 4 is a BET plot for SWISH based on the GVS data in FIG. 2
Figure 5:
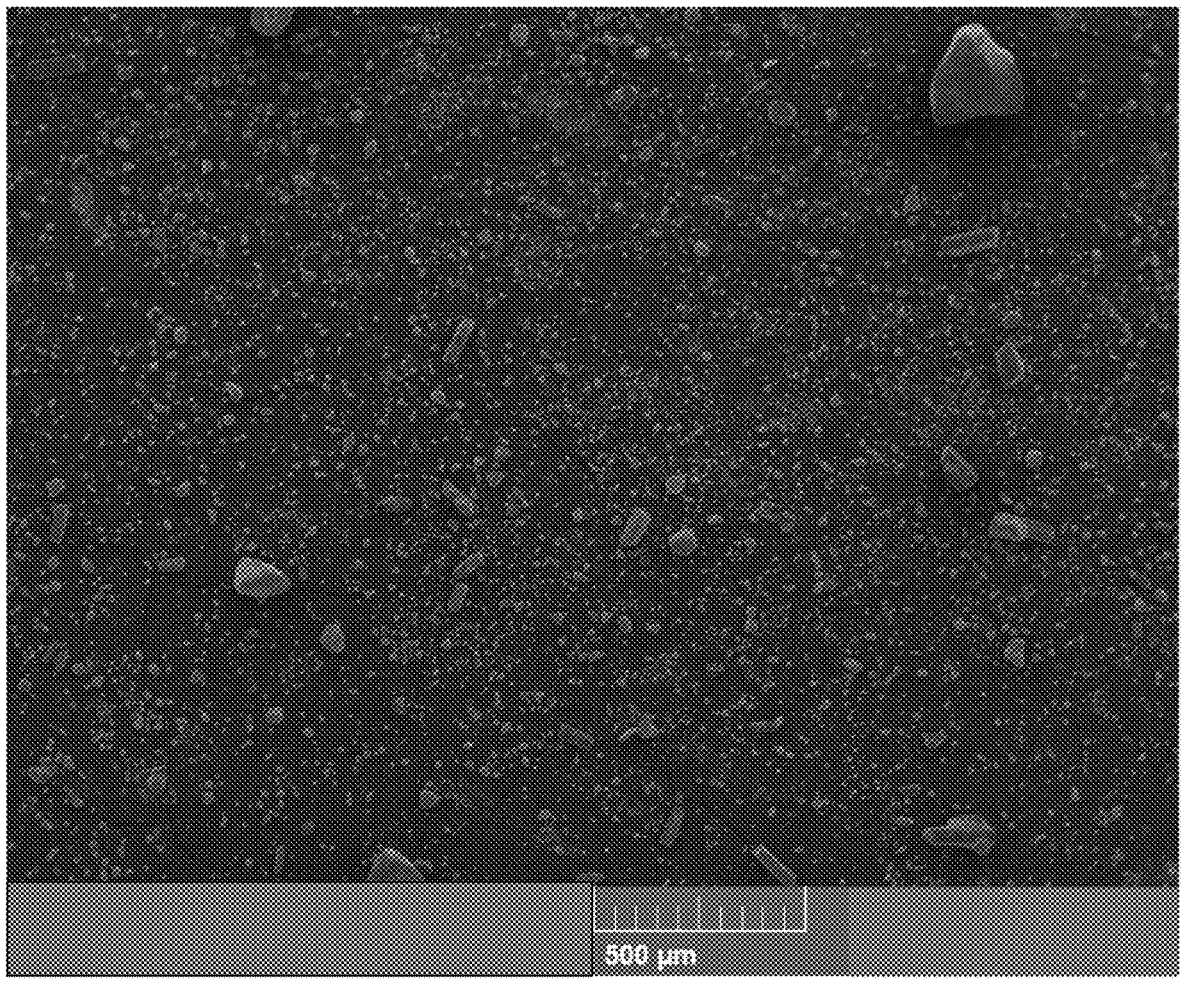
FIG. 5 is a scanning electron micrograph of WOW Pink
Figure 6:
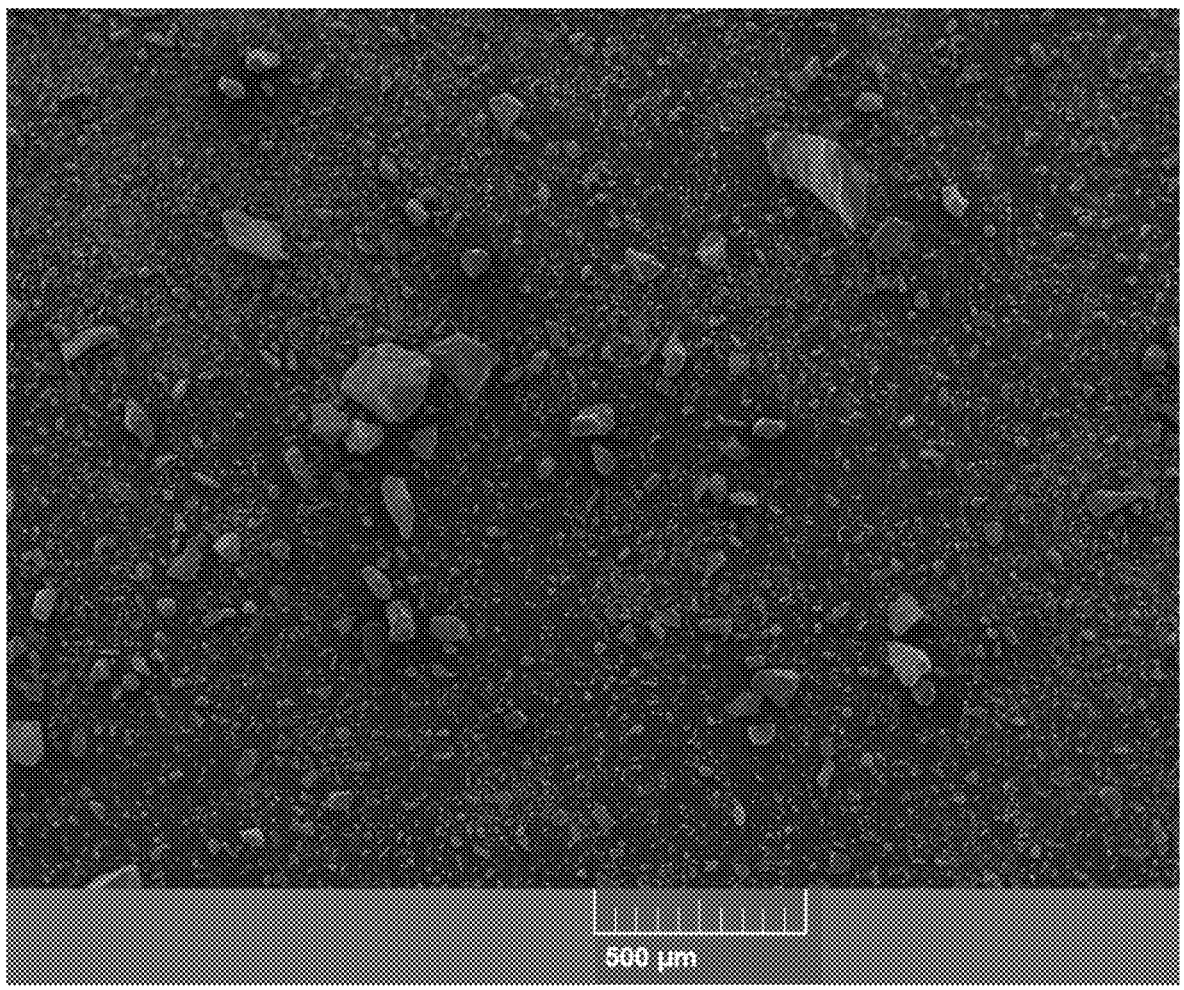
FIG. 6 is a scanning electron micrograph of SWISH

Preparation of a Powder Oral Hygiene Composition According to the Invention.

A powder oral hygiene composition according to the invention was prepared using the following ingredients in the stated proportion:

|  | SWISH |
| --- | --- |
| Xylitol | 84.03% |
| Citric acid | 1.13% |
| Silicon dioxide (J M Huber, Zeodent ® 113) | 6.76% |
| Sodium bicarbonate | 7.99% |
| 1-menthol | 0.025% |
| Spearmint flavour | 0.087% |
|  | 100 |

Prior to blending, all the components, save for the silicon dioxide, were milled and then sieved through a 60# US Mesh screen, equivalent to a 325 micron particle size. The silicon dioxide, Zeodent® 113, manufactured by J M Huber which has a median particle size of 10-15 microns, was then added and blending completed in a V blender. The use of a V blender minimises friction and internal heating of the powder during the blending process. Blending was continued for about 15 minutes.

Prior Art Product—WOW Pink

WOW Pink is made from the identical ingredients to those disclosed above for SWISH and with broadly similar proportions. The formulation is also broadly similar to that disclosed in US 2015/0004560, composition #2, powder oral rinse, save that the sorbitol has been replaced by xylitol, to increase the total xylitol to about 85% w/w.

However, the preparation of the WOW product is different to that of the present invention, in that there is no sieving of the ingredients prior to blending. Furthermore, the ingredients are mixed in a dry ribbon blender, with one half of the amount of xylitol, then the other ingredients added in a bulk and the blender run at a medium rate for less than 5 minutes, and then the remainder of the xylitol is added and the resulting mixture blended for about 10-20 minutes. The resulting white powder is put into polythene lined drums, purged and sealed under nitrogen.

The resulting product is packed into stick packs and sealed under nitrogen.

Gravimetric Vapour Sorption

Approximately 50 mg of sample was placed into a wire-mesh vapour sorption balance pan and loaded into an 'IgaSorp' vapour sorption balance (Hiden Analytical Instruments). The sample was dried by maintaining a 0% humidity environment until no further weight change was recorded (maximum drying time 2 hrs). The sample was then subjected to a ramping profile from 0-40% RH at 5% RH increments, maintaining the sample at each step until equilibration had been attained (99% step completion or a maximum of two hours). Upon reaching equilibration, the percentage RH within the apparatus was ramped to the next step and the equilibration procedure repeated.

The Hydrophilic/Water surface area was then calculated by applying the BET equation to the isotherm obtained. For the prior art product WOW Pink, the Water Surface Area (WSA) was determined to be 97.757 $m^2/g$. For product according to the invention, SWISH, the WSA was determined to be 180.484 $m^2/g$.

These results suggest that the product according to the invention, SWISH, will be significantly more wettable than the prior art product, WOW Pink and so more acceptable to consumers. In particular, the product has improved mouth feel compared to the prior art product, WOW Pink.

The invention claimed is:

1. A powder oral hygiene composition comprising:
   xylitol,
   a source of carbon dioxide,
   an acid, and
   an absorbent,
      wherein the xylitol is from 80 wt % to 95 wt % of the composition;
      wherein the composition has a water surface area greater than 160 $m^2/g$; and
      wherein the composition can pass through a 250 micron sieve.

2. A composition according to claim 1, wherein the carbon dioxide source is from 3 wt % to 20 wt % of the composition.

3. A composition according to claim 1, wherein the absorbent is from 0.5 wt % to 20 wt % of the composition.

4. A composition according to claim 1, wherein the acid is from 0.5 wt % to 15 wt % of the composition.

5. A composition according to claim 1, comprising from about 3 wt % to about 20 wt % of a carbon dioxide source, from about 0.5 wt % to about 20 wt % of an absorbent and from 0.5 wt % to about 15 wt % of an acid.

6. A composition according to claim 1, wherein the carbon dioxide source is sodium bicarbonate.

7. A composition according to claim 1, wherein the absorbent is silica dioxide.

8. A composition according to claim 1, wherein the acid is citric acid.

9. A composition according to claim 1, comprising from about 3 wt % to about 20 wt % of a carbon dioxide source, wherein the carbon dioxide source is sodium bicarbonate.

10. A composition according to claim 1, comprising from about 0.5 wt % to about 20 wt % of an absorbent, wherein the absorbent is silica dioxide.

11. A composition according to claim 1, comprising from about 0.5 wt % to about 15 wt % of an acid, wherein the acid is citric acid.

12. A composition according to claim 1, comprising from about 3 wt % to about 20 wt % of a carbon dioxide source.

13. A composition according to claim 1, comprising from about 3 wt % to about 20 wt % of a carbon dioxide source and from about 0.5 wt % to about 15 wt % of an acid.

14. A composition according to claim 1, comprising from about 3 wt % to about 20 wt % of a carbon dioxide source, from about 0.5 wt % to about 20 wt % of an absorbent and from 0.5 wt % to about 15 wt % of an acid.

15. A composition according to claim 1, comprising from about 3 wt % to about 20 wt % of a carbon dioxide source, from about 0.5 wt % to about 20 wt % of an absorbent and from 0.5 wt % to about 15 wt % of an acid, wherein the carbon dioxide source is sodium bicarbonate, the absorbent is silica dioxide and the acid is citric acid.

* * * * *